United States Patent [19]

Tam

[11] Patent Number: 4,922,421

[45] Date of Patent: May 1, 1990

[54] FLAW CHARACTERIZATION BY MULTIPLE ANGLE INSPECTION

[75] Inventor: Kwok C. Tam, Schenectady, N.Y.

[73] Assignee: General Electric Company, Schenectady, N.Y.

[21] Appl. No.: 270,973

[22] Filed: Nov. 14, 1988

Related U.S. Application Data

[63] Continuation of Ser. No. 941,875, Dec. 15, 1986.

[51] Int. Cl.⁵ .............................................. G06F 15/42
[52] U.S. Cl. ......................... 364/413.25; 364/413.13; 378/901
[58] Field of Search ...................... 364/413.13, 413.19, 364/413.2, 413.21; 378/901

[56] References Cited

U.S. PATENT DOCUMENTS 4,506,327 3/1985 Tam ................................ 364/413.19

OTHER PUBLICATIONS

Tam, "Two-Dimensional Inverse Born Approximation in Ultrasonic Flaw Characterization", 1985.
Tam et al., "Limited Angle Three Dimensional Reconstruction Using Fourier Transform Iterations and Radon Transform Iterations", 1981.

Primary Examiner—Joseph Ruggiero
Assistant Examiner—Kim Thanht Bui
Attorney, Agent, or Firm—John S. Beulick; James C. Davis, Jr.; Paul R. Webb, II

[57] ABSTRACT

Flaw uniform density location and size for flaws smaller than the beam diameter of an ultrasound beam are determined by measurement of return echos of ultrasound. The return echos are transformed to Fourier space and are normalized to take away any dependence upon factors other than the flaw in the object under test. The Fourier space representation of the return echo after normalization is dependent on a flaw characteristic function. The flaw characteristic function is repeatedly transformed between object space and Fourier space in order to eliminate or minimize errors in the flaw characteristic function. In frequency or Fourier space, the flaw characteristic function is reset to take into account the known Fourier components derived from the return echo waveforms, whereas the object space flaw characteristic function is corrected to take into account the fact that the flaw characteristic function has only two values, 0 and 1.

3 Claims, 5 Drawing Sheets

FLAW CHARACTERIZATION BY MULTIPLE ANGLE INSPECTION

This application is a continuation, of application Ser. No. 941,875, filed 12/15/86.

BACKGROUND OF THE INVENTION

This invention relates to a method of flaw characterization by multiple angle inspection using ultrasound and a limited-angle reconstruction procedure.

Ultrasound is frequently used to locate and characterize flaws in nondestructive testing. However, present state-of-the-art techniques generally do not allow one to determine the identity, shape, and orientation of a flaw if its size is smaller than the ultrasound beam diameter. The current accuracy of the size and composition estimates of a flaw depends on the ratio of the characteristic size of the flaw to the beam diameter. For a flaw having a size larger than the beam diameter, its dimension can be estimated by laterally scanning an acoustic microscope around the flaw location in what is usually referred to as a c-scan. However, this c-scan estimation is not practical for a flaw having a size smaller than the beam diameter. Instead, composition and geometrical parameters of these flaws are often estimated from the acoustic scattering pattern.

Flaw characterization is an inversion problem in which the parameters of the flaw such as its type, elastic constants, shape, size, orientation, etc., are deduced from the scattering amplitude measurements. In general, no explicit expression of flaw parameters in terms of scattering amplitudes is available. The relation between the scattering amplitude of the acoustic waves and the flaw parameters can be expressed by the integral equation in tensor notation as developed in Gubernatis, J.E., Domany, E and Krumhansl, J.A., "Formal Aspects of the Theory of the Scattering of Ultrasound by Flaws in Elastic Materials", J. Appl. Phys., 48 (1977) 2804. The exact solution for the integral equation for general cases does not yet exist. As a result, one has to resort to particular cases and approximation methods. In the three-dimensional inverse Born approximation, it can be shown that for incident plane wave and for isotropic homogeneous medium and flaw, the back-scattered amplitude $A(\omega, \Omega)$ can be written in the form:

$$A(\omega,\Omega) = \omega^2 F(\{\mu\}) S(2\omega/v, \Omega) \quad (1)$$

Where F is a function of $\{\mu\}$ which denotes collectively the material parameters of the medium and the flaw, and S is equal to the Fourier transform of the characteristic function of the flaw in the direction $\Omega$ of the incident plane wave, Rose, J.H. and Krumhansl, J.A., "Determination of Flaw Characteristics from Ultrasonic Scattering Data", J. Appl. Phys., 50 (1979) 2951. The characteristic function as defined is equal to 1 inside the flaw and equal to 0 outside the flaw. From equation (1) one obtains S as follows:

$$S(\omega/v,\Omega) = 4A(\omega/2,\Omega)/[\omega^2 F(\{\mu\})] \quad (2)$$

The Fourier transform of the flaw characteristic function therefore can be obtained by superimposing the quantity S in all incident directions and from which the characteristic function itself can be reconstructed by inverse Fourier transformation. The Lame material constants of the flaw can also be obtained in the process.

In general, it is not feasible to inspect a flaw from all incident angles. As a result, the Fourier transform of the characteristic function would have missing components in some angular range. These missing components give rise to artifacts in the reconstructed characteristic function. Partly because of the impracticality of viewing from all incident directions and partly because of the complexity of the three-dimensional reconstruction procedure, the method is usually simplified and restricted to characterize the class of ellipsoidally shaped flaws. For this class of flaws, one can obtain all relevant information about the flaw from a small number of back-scattered waveforms. This significantly simplifies the application of the procedure. This simplified procedure is known as the one-dimensional inverse Born approximation, see Rose, J.H., Eisley, R.K., Tittman, B., Varadan, V.V., and Varadan, V.K., "Inversion of Ultrasonic Scattering Data", in Acoustic, Electromagnetic and Elastic Wave Scattering, V.V. Varadan and V.K. Varadan (Eds.), Pergamon, N.Y., 1980. Though the procedure is simple, it cannot be applied to characterize flaws of general shape.

Limited-angle reconstruction techniques have been developed to remove artifacts due to missing information. Such techniques are discussed, for example, in Tam, K.C., and Perez-Mendez, V., "Tomographical Imaging with Limited-Angle Input", J. Opt. Soc. Am., 71 (1981) 582, coauthored by the present inventor. Typically, the limited-angle image reconstruction techniques make use of available a priori information of the object to compensate for the missing information that is due to restrictions on the scan. The most readily available a priori information include the external boundary of the object, and the known upper and lower bounds of the density values. Greater precision in knowledge of the a priori information provides better quality in the reconstructed images of the object which is being inspected. However, the images reconstructed in this way are usually not as good as images reconstructed from complete angular scanning information.

A method for improvement of images reconstructed from limited-angle information makes use of multiple energy x-ray scanning as taught in the inventor's Patent 4,506,327 entitled "Limited-Angle Imaging Using Multiple Energy Scanning". The method is for composite objects, such as industrial products and equipment, which are made of a small number of substances. The object is scanned several times by x-rays at different energies. By suitably combining the scanning data, the different components within the object can be constructed individually to result in much better image quality. However, the method cannot be used if it is impractical to perform multiple energy x-ray scannings.

SUMMARY OF THE INVENTION

A general object of the present invention is to provide an improved flaw characterization method.

A more specific object is to provide a flaw characterization method using an improved limited-angle reconstruction procedure to provide more accurate information of a flaw having a general shape.

Yet another object of the present invention is to provide a flaw characterization technique which efficiently uses limited-angle reconstruction procedures to supply missing information over an angular range.

Generally, the method of the present invention uses ultrasound pulses to generate a flaw characteristic function, which flaw characteristic function has a value of 0 outside of a flaw and 1 inside of the flaw. The flaw characteristic function has missing Fourier components which are recovered by repeated transformations of iterates of the flaw characteristic function between the object space and the Fourier space. By use of the knowledge that the flaw characteristic function only has the values 0 and 1, the limited-angle reconstruction procedure may more accurately characterize the shape and size of the flaw.

The above and other objects of the present invention which will become more apparent as the description proceeds are more specifically realized by a method of flaw characterization for flaws of general shape and uniform density comprising the steps of: taking pulse echo measurements and acquiring a plurality of return echo waveforms from pulses of ultrasound incident on a flaw in an object at a plurality of angles within an allowed angular range; Fourier transforming the echo waveforms and generating a plurality of lines of known Fourier components of a flaw characteristic function which specifies the shape of the flaw, the flaw characteristic function defined in the object space as having a value of 1 inside a flaw and 0 outside the flaw, each of the lines corresponding to one of the angles within the allowed angular range; orienting the lines at their corresponding angles and superimposing the lines to form a threedimensional Fourier transform based on the limited angle information of the flaw characteristic function; and recovering missing Fourier components of the flaw characteristic function by a limited-angle reconstruction procedure including repeated transformations of iterates of the flaw characteristic function between object space and Fourier space, the procedure correcting the values of object space iterates of the flaw characteristic function based on a priori information as to the extent and location of the flaw and the requirement that the characteristic function has no value above 1 and no value below 0, and the procedure correcting the Fourier space iterates of the flaw characteristic function by resetting components to the known Fourier components.

The procedure repeatedly transforms iterates of the flaw characteristic function between object space and Fourier space by three-dimensional inverse fast Fourier transforms. The procedure operates on values of the object space iterates of the flaw characteristic function by setting all values to be 0 or 1. More specifically, the procedure resets to 0 those values which are between 0 and 0.5 and resets to 1 those values which are between 0.5 and 1. The lines of known Fourier components of the flaw characteristic function are generated by first dividing the Fourier transformed echo waveforms by the square of the angular frequency of the ultrasonic wave. The method further comprises the following normalization procedure and the steps of dividing by the strength of the incident ultrasound wave, dividing by the transmission coefficient at an interface between the object and a liquid in which the object is disposed, and dividing by a function of the material properties of the object and the flaw, and multiplying by a factor of 4. The entire normalization procedure needs to be applied to only one echo waveform, and all the other echo waveforms are normalized by comparison to the first one. The procedure further operates on values of the object space iterates of the flaw characteristic function by: resetting to 0 those values which are outside the known extent of the object, resetting to 1 those values which are higher than 1, and resetting to 0 those values which are negative.

The present invention may alternately be described as a method of flaw characterization for flaws of general shape comprising the steps of: taking pulse echo measurements and acquiring a plurality of return echo waveforms from ultrasound pulses applied to a flaw in an object by at least one transducer, the ultrasound pulses being applied at a plurality of angles within an allowed angular range; Fourier transforming the echo waveforms; dividing the Fourier transformed echo waveforms by the square of the angular frequency of the ultrasonic wave; normalizing a first one of the Fourier transformed echo waveforms as described above, and normalizing all the others by comparison to the first one, and generating a plurality of lines of known Fourier components of the flaw characteristic function; orienting the lines at their corresponding angles and superimposing the lines to form a three-dimensional Fourier transform based on the limited-angle information of the flaw characteristic function; and recovering missing information about the flaw characteristic function by a limited-angle reconstruction procedure including repeated transformation of iterates of the flaw characteristic function between the object space and another space, the procedure correcting the values of object space iterates of the flaw characteristic function based on a priori information as to the extent and location of the flaw and the requirement that the flaw characteristic function has no value above 1 and no value below 0, and the procedure correcting each iterate of the flaw characteristic function in the other space based upon information from the echo waveforms. The other space is Fourier space.

The present invention may alternately be described a method of flaw characterization for flaws of general shape and uniform density comprising the steps of: taking pulse echo measurements and acquiring a plurality of return waveforms from pulses of ultrasound incident on a flaw in an object at a plurality of angles in an allowed angular range; Fourier transforming the echo waveforms and generating a plurality of lines of known Fourier components of the flaw characteristic function, each of the lines corresponding to one of the angles within the allowed angular range; orienting the lines at their corresponding angles and superimposing the lines to form a three-dimensional Fourier transform based on the limited-angle information of the flaw characteristic function; and recovering missing information about the flaw characteristic function by a limited-angle reconstruction procedure including repeated transformations of iterates of the flaw characteristic function between the object space and another space, the procedure correcting values of the object space iterates of the flaw characteristic function by: resetting to 0 those values which are between 0 and 0.5, resetting to 1 those values which are between 0.5 and 1, and the procedure correcting each iterate of the flaw characteristic function in the other space based upon information from the echo waveforms. The other space is Fourier space.

BRIEF DESCRIPTION OF THE DRAWINGS

FIG. 1a shows the density of a general object of one dimension, whereas

DETAILED DESCRIPTION OF THE INVENTION

Figure 1A:
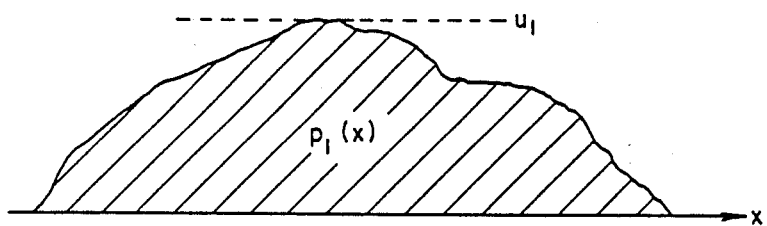
Figure 1B:
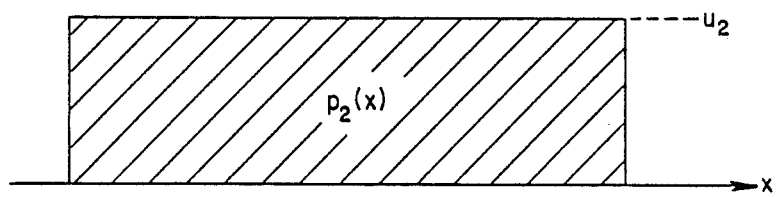
FIG. 1b shows the density of a one dimensional object with uniform density.

FIGS. 1a and 1b show two functions which may be used in explaining a principle of this invention. In particular, FIG. 1a shows the density function $p_1(x)$ of a one-dimensional object having a non-uniform density. As shown, the density may vary between an upper limit $u_1$ and a 0 density. If one attempts to reconstruct the object of FIG. 1a from limited-angle scanning information, the knowledge that the density function must be between 0 and $u_1$ produces only minor or insignificant improvement in trying to reconstruct the density function of the object from limited-angle information. More specifically, the function only has the values $u_1$ and 0 at a very small portion of its range.

If one scanned the object of FIG. 1a from a limited angular range and developed representations of Fourier components of the density function of the object, one could then perform an inverse Fourier transform and develop an estimate of the density in the object space. However, the knowledge that the density function must be between 0 and $u_1$ would not allow one to improve the representation of the density function greatly. The limited-angle information might provide a density function which deviated greatly from that shown in FIG. 1a (the actual density function of the object), but one would not know to correct it except by resetting values above $u_1$ to $u_1$ and by resetting values below 0 to 0. The limited information about the possible functional values does not provide great help in correcting for the limited-angle information by using the information in the object space.

FIG. 1b shows a function such as a density function $p_2(x)$ of a one-dimensional object having a uniform density. For such an object, the density function has the value of $u_2$ within the object and 0 outside of the object. Because the function can only have two values, image reconstruction using an iteration process may provide much more significant improvement than would be the case for a function such as that illustrated in FIG. 1a. The significant improvement in image reconstruction from incorporating the boundary information for the function of FIG. 1b (see, Tam, K.C., "The Use of Multispectral Imaging in LimitedAngle Reconstruction", IEEE Trans. Nucl. Sci., NS-29 (1982) 512 authored by the present inventor) results from the fact that the function $p_2$ is equal to $u_2$ within a closed region, there being no region with density values between 0 and $u_2$. Values above $u_2$ may be reset to $u_2$ and values below 0 may be reset to 0 to yield better results than with the $p_1(x)$ function. Quite significantly, one can also reset intermedite values (between 0 and $u_2$) either to $u_2$ or 0 according to which level it is closer to, thereby eliminating most of the errors in reconstruction.

Figure 2:
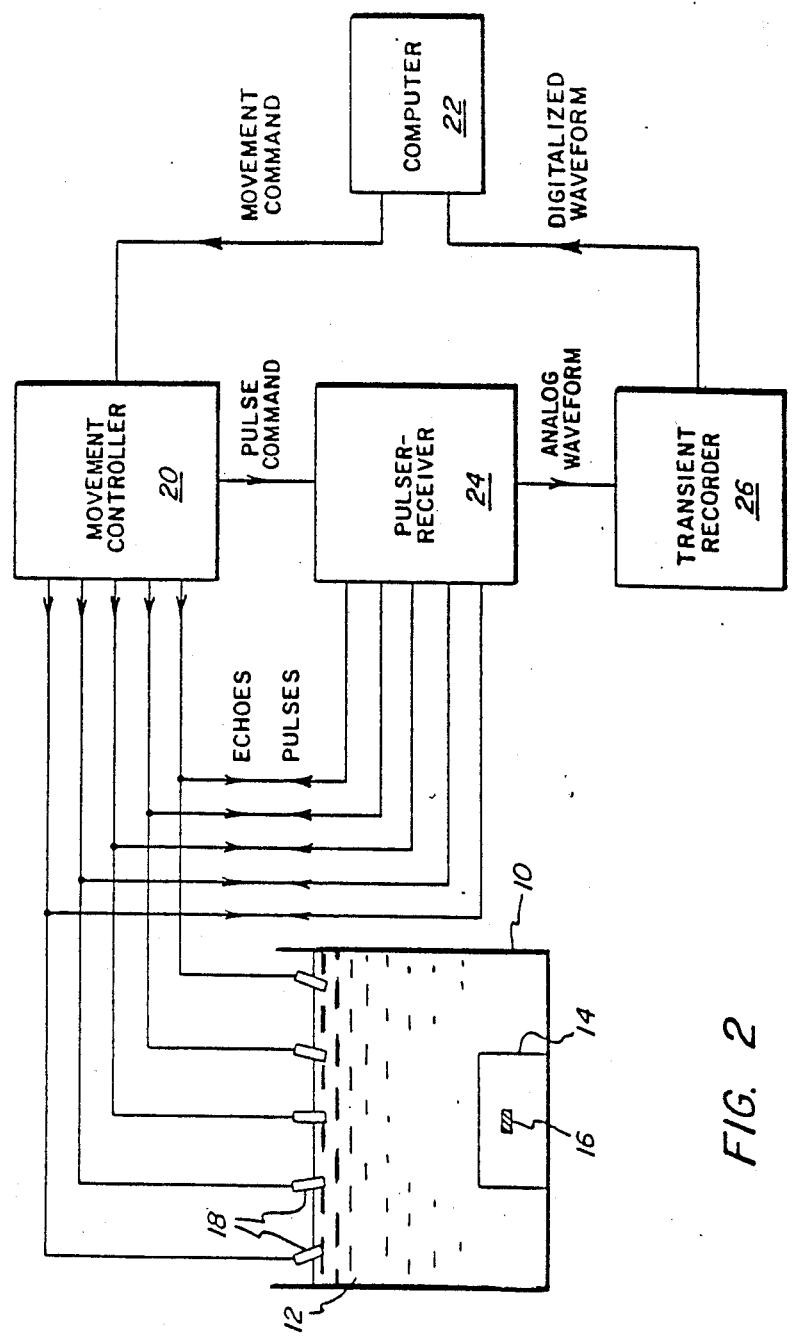
FIG. 2 shows a schematic of a system used to carry out the method of the present invention.

FIG. 2 shows a practical realization of apparatus used for carrying out the method of the present invention. In particular, a container 10 is filled with a liquid such as water 12 and has an object 14 which is to be tested for flaws. A flaw 16 has been illustrated within the material 14. A series of unfocused matching transducers 18 are used for applying and receiving ultrasonic pulses. The transducers 18 are mounted upon mechanical arms (not illustrated) which are controlled by a movment controller 20. The movement controller 20 moves the transducers around and tilts them at different angles, and is preferably a microprocessor controlled by signals sent from the signal processing computer 22. The transducers are moved on their mechanical arms and stabilized in a particular position. The movement controller sends a signal to start a pulser-receiver 24 whose pulses activate the transducers 18. The return echoes from the flaw are detected by the transducers, sent to the pulser-receiver 24, and then to a transient recorder 26 which digitizes the waveforms for input to the signal processing computer 22. The various components shown by FIG. 2 are well known and detailed discussion of their particulars is not necessary.

Figure 3:
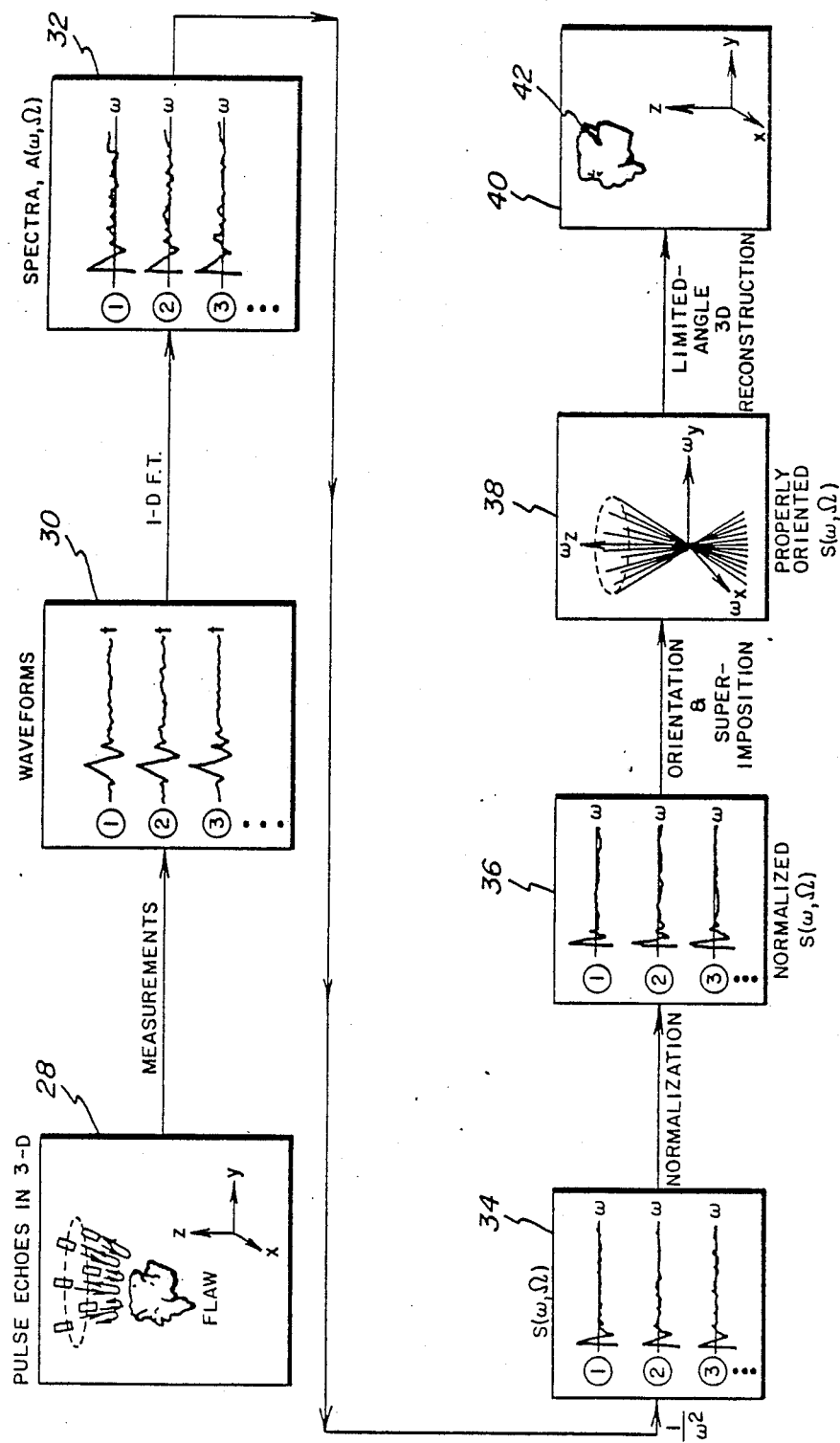
FIG. 3 shows a summary of the method of the present invention.

FIG. 3 shows a block diagram of the overall process of the present invention. In block 28, the transducers 18 are arranged in a circle and have pulsed the object 14 repeatedly and have received pulse echoes in three dimensions. The computer 22 and pulser-receiver 24 have provided preferably several hundred pulses and detected corresponding pulse echoes. Each of the pulse echoes is a time domain signal corresponding to the back-scattered amplitude for a particular angle $\Omega$. The time-domain amplitude signals illustrated in block 30 are each subjected to a one-dimensional Fourier transform to yield the corresponding spectra $A(\omega, 106)$ in block 32. Each of the spectra of block 32 is divided by $\omega$ squared so as to generate the spectra of the characteristic function S at block 34. The angular frequency is known.

The spectra of block 34 are then normalized to generate the spectra of block 36. In order to normalize the spectra of block 34, (1) one of the spectra is divided by the strength of the incident plane wave, divided by the transmission coefficient at the interface between the material of object 14 and the liquid such as water in which the object is immersed, divided by the function F, and multiplied by a factor 4; (2) each of the rest of the spectra is scaled such that its D.C. component is equal to that of the spectrum normalized in (1), as described in Tam, K.C., "Two-Dimensional Inverse Born Approximation in Ultrasonic Flaw Characterization," J. Nondestr. Eval. 5 (1985) 95, authored by the present inventor. The strength of the incident plane wave at each frequency can be readily obtained from the Fourier transform of the waveform back-scattered from a flat surface immersed in water in known fashion, the transmission coefficients can be calculated theoretically, as described in Adler, L. et al "Identification of Flaws from Scattered Ultrasonic Fields as Measured at a Planar Surface", Proc. ARPA/AFML Review of Progress in Quantitative NDE, May 1978, Science Center, Rockwell International, AFML-TR-78-55, p.36, and the functional value of F can be readily obtained from the measurements of the scattering amplitudes in the long-wavelength limit where the quantity $S(\omega, \Omega)$ goes to a constant as $\omega$ goes to zero (equation 1 may be used in this calculation). The calculation is discussed in the Rose article cited above. The normalized spectra of block 36 would then correspond to the characteristic function S of equation 2. However, the spectra are incomplete because we are missing information corresponding to missing angles in the application of pulses to the flaw 16. In other words, a limitation on our ability to pulse the flaw from particular angles in the object space corresponds to an absence of particular Fourier space frequency components in the characteristic function S of block 36.

The characteristic function spectra of block 36 will then be oriented and superimposed to provide a three-dimensional representation of the Fourier space characteristic function S as shown in block 38. However, the Fourier space characteristic function of block 38 is incomplete due to the missing angle components. In order to supplement the lines of known Fourier components of block 38, a limited-angle 3D reconstruction procedure is performed to fill in the missing Fourier information and to inverse transform the completed Fourier transform of the characteristic function to the object space to provide an object space representation of the flaw 42 within block 40. The object space representation of flaw 42 is three-dimensional so that it can be viewed from different angles by use of computerized image manipulation.

Figure 4:
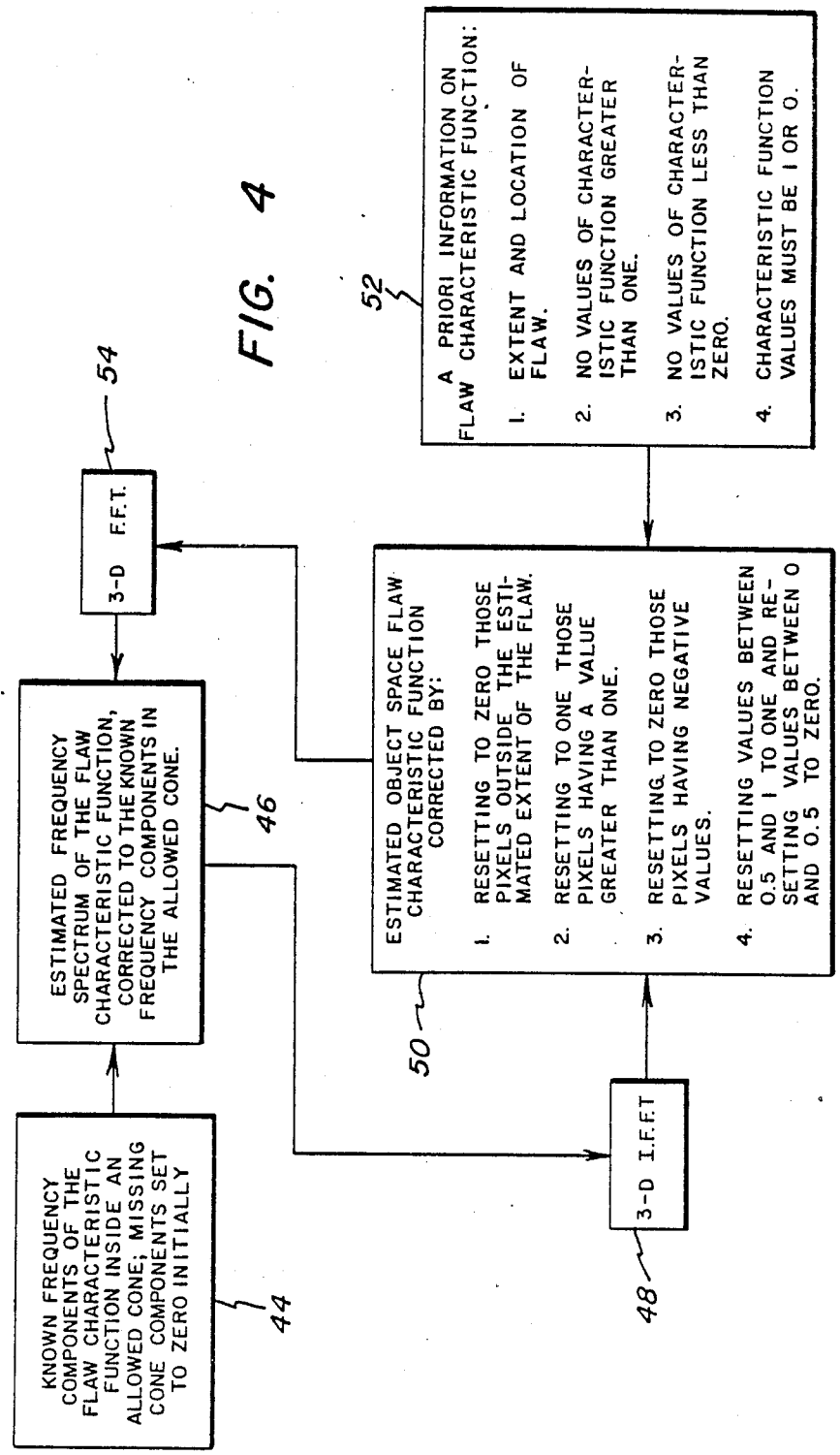
FIG. 4 shows a limited-angle reconstruction technique as used with the present invention.

FIG. 4 shows the limited-angle reconstruction procedure used by the present invention to recover missing Fourier components of the flaw characteristic function of block 38 of FIG. 3. Initially, we have the known frequency components of the flaw characeristic function inside an allowed cone as represented in block 44 of FIG. 4. These known frequency components are schematically illustrated in the block 38 of FIG. 3. The frequency components from a missing cone are set to 0 initially.

The Fourier space flaw characteristic function of block 44 is provided as shown in block 46 as an estimated frequency spectrum of the flaw characteristic function. A first iterate simply uses the initial known lines of Fourier components from the pulse echo waveforms. This first iterate of the Fourier space flaw characteristic function is carried from block 46 to block 48 wherein a three-dimensional inverse fast Fourier transform is performed. This converts the Fourier space flaw characteristic function first iterate into a first iterate object space flaw characteristic function in block 50. This first iterate object space flaw characteristic function is corrected to take into account certain a priori information provided as indicated at block 52.

As shown in block 52, we have an estimate as to the extent and location of the flaw (the procedure for obtaining this estimate is discussed below). We know by definition that the flaw charactristic function has no values greater than 1 and has no values less than 0. Additionally, we know that the flaw characteristic function values must be either 1 or 0. Accordingly, block 50 will take the first iterate of the object space flaw characteristic function and correct it by resetting to 0 those values which are outside of the estimated extent of the flaw. (For discussion purposes only, reference is made to pixels in block 50 as one will ordinarily want to display the values). Block 50 also indicates that the values of the function or pixels having a value greater than 1 are reset to 1 and values less than 0 are reset to 0. Further, block 50 indicates that the values of the characteristic function which are between 0.5 and 1 are reset to 1 and the values between 0 and 0.5 are reset to 0 in light of our knowledge that the characteristic function must have either one of these two values.

The object space flaw characteristic function which has been corrected by the steps of block 50 is then subject to a three-dimensioned fast Fourier transform in block 54 which converts it back into the Fourier or frequency space block 46. By virtue of the corrections which have been performed in block 50, the error in the Fourier space flaw characteristic function has been reduced. However, the error has also been reallocated in that the corrections of block 50 will likely have caused some of the known Fourier components to deviate from their proper values. Accordingly, block 46 will reset those known Fourier components to their proper and original values corresponding to the measurements which were taken over the allowed angular range of measurement of the flaw. This will further reduce the error in the Fourier space flaw characteistic function, which is then inverse Fourier transformed by block 48 and returned as a further iterate of the object space flaw characteristic function corrected by the procedure of block 50 for return to block 46 by way of block 54.

The cycling between the object space and Fourier space continues in the loop illustrated by blocks 46, 48, 50, and 54 with repeated transformations of iterates of the flaw characteristic function between object, space and Fourier space until the flaw characteristic function is sufficiently precise and accurate that it may be viewed or otherwise stored in a computer as the accurate representation of the shape and size of a particular flaw. As will be readily appreciated, the blocks of FIG. 4 are illustrative of the procedure, which procedure would preferbly be carried out by a computer. Preferably, the procedure will cycle through 10 to 20 complete cycles corresponding to 10 to 20 frequency space iterates in order to generate a sufficiently accurate flaw characteristic function, although the number of cycles could readily deviate from this range. Alternately, one could check for convergence of the flaw characteristic function and use such a check to stop the cyling. For example, if the flaw characteristic function changes less than a particular percentage between one iteration and the next iteration, this could be used as a signal that the procedure has been carried out a sufficient number of cycles to provide an acceptable representation of the flaw characteristic function.

It should be noted that block 50 indicates the resetting of values between 0 and 0.5 to 0, but does not indicate what the computer should do with values which are exactly 0.5. Although it is highly unlikely that values would be developed which are exactly 0.5, the computer could readily be programmed to look at the neighborhood of values immediately around such a value and to round the value up to 1 if the average of neighborhood values was above 0.5 and to round the value down to 0 if the neighborhood of values was below 0.5.

Figure 5:
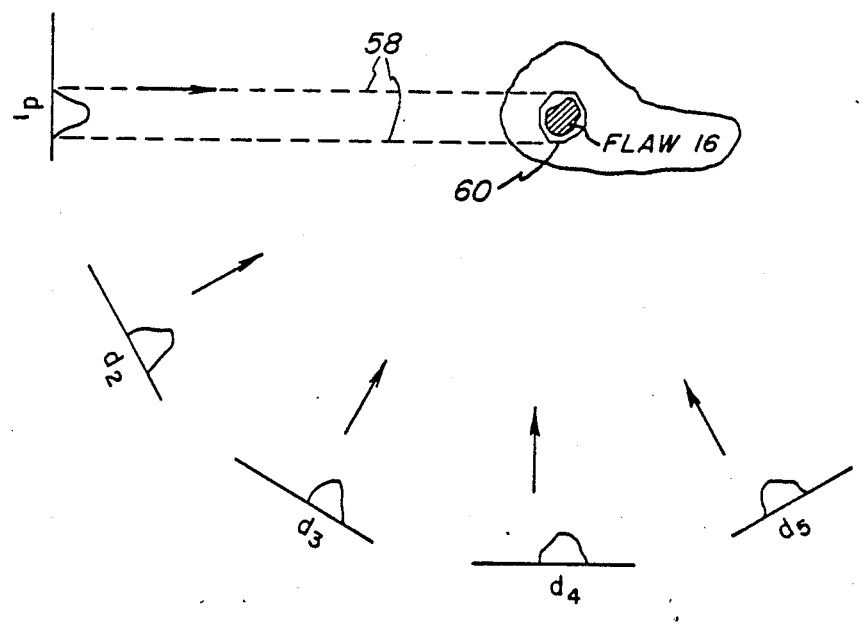
FIG. 5 shows a technique which may be used to develop information about the boundaries of the flaw.

FIG. 5 illustrates a principle which may be used to derive the extent and location of the flaw for block 52 of FIG. 4. In particular, FIG. 5 shows a series of projections d1, d2, d3, d4 and d5. Each of the projections corresponds to a particular line of the characteristic function shown in block 36 of FIG. 3. In particular, each of the projections can be obtained by applying a one-dimensional inverse fast Fourier transform to each line of block 36. The back projections then represent the two planes within which the flaw must be located. The planes are constructed by: (1) drawing lines (such as lines 58 shown for $d_1$ only) from the edges of the back projections in the direction of the pulse ($\Omega$); (2) forming the planes from the lines by sweeping the lines perpendicularly out of and into the plane of the paper. Through such back projection constructions one realizes a boundary 60 within which the flaw must be located. This boundary 60 may then be used to limit the outer extent of the flaw characteristic function. That is, any value of the flaw characteristic function outside of the boundary 60 will be corrected by resetting to 0 as Step 1 of block 50 in FIG. 4.

The back projection arrangement of FIG. 5 is similar to a back projection arrangement described, together with an iteration back projection limited-angle reconstruction procedure, in more detail in the present inventor's copending application S.N. 877,083, entitled "Method for Reconstructing Objects From Limited-Angle Scannings In Computerized Tomography", filed June 23, 1986, now abandoned, and in continuation application Ser. No. 205,398, filed June 10, 1988 except that the back projections are generated by use of a hypothetical flawless object in the other application. That application is hereby incorporated by reference.

While the invention has been shown and described with reference to a preferred embodiment, it will be understood by those skilled in the art that various changes in form and details may be made without departing from the spirit and scope of the invention. The scope of the invention should be determined by reference to the claims appended hereto.

What is claimed is:

1. A method of flaw characterization for three-dimensional flaws of general shape and uniform density, said method comprising the steps of:

(a) obtaining echo waveforms from pulses of ultrasound incident on a flaw in an object, the ultrasound pulses being incident on the flaw at a plurality of angles within an allowed limited angular range;

(b) Fourier transforming said echo waveforms and generating a plurality of lines of known Fourier components of a flaw characteristic function which specifies the shape of the flaw, the Fourier components being defined in object space as having a value of 1.0 inside the flaw and zero outside the flaw, each of said lines corresponding to one of said angles within the allowed limited angular range;

(c) orienting the lines of known Fourier components at their corresponding angles and superimposing the lines to form a three-dimensional Fourier transform based on limited-angle information of the flaw characterization function; and (d) recovering missing information about the flaw characteristic function and providing a three-dimensional object space representation of the uniform density flaw by an iterative limited-angle reconstruction procedure including repeated transformations of iterates of the flaw characteristic function between the object space and Fourier space, the reconstruction procedure correcting values of the flaw characteristic function in the object space based on a priori information including that the flaw characteristic function must be 1.0 or zero, said reconstruction procedure comprising the steps of resetting to zero those values outside a known extent of the flaw, resetting to 1.0 those values of the flaw characteristic function which are higher than 1.0, resetting to zero those values which are negative, resetting to zero those values which are between zero and 0.5, and resetting to 1.0 those values which are between 0.5 and 1.0; and the reconstruction procedure correcting the Fourier components of the flaw characteristic function in the Fourier space based on information from the echo waveforms.

2. A method in accordance with claim 1 wherein said limited angle reconstruction procedure repeatedly transforms the iterates of the flaw characteristic function between the object space and Fourier space by three-dimensional fast Fourier transforms and three-dimensional inverse fast Fourier transforms.

3. A method in accordance with claim 1 further comprising, in step b, dividing the Fourier transformed echo waveforms by ultrasound frequency squared, and normalizing a first one of said Fourier transformed echo waveforms and normalizing all others by comparison to the first one.

* * * * *